(12) United States Patent
Schäfer et al.

(10) Patent No.: US 6,930,103 B2
(45) Date of Patent: Aug. 16, 2005

(54) USE OF VASOPEPTIDASE INHIBITORS IN THE TREATMENT OF METABOLIC DISEASES, NEPHROPATHY AND ADVANCED GLYCATION END-PRODUCT ASSOCIATED DISEASES

(75) Inventors: Stefan Schäfer, Sulzbach (DE); Wolfgang Linz, Mainz (DE); Markus Bleich, Hünfelden-Dauborn (DE); Jochen Huber, Maxdorf (DE)

(73) Assignee: Aventis Pharma Deutschland GmbH, Frankfurt (DE)

( * ) Notice: Subject to any disclaimer, the term of this patent is extended or adjusted under 35 U.S.C. 154(b) by 15 days.

(21) Appl. No.: 10/607,521

(22) Filed: Jun. 26, 2003

(65) Prior Publication Data

US 2004/0058911 A1 Mar. 25, 2004

Related U.S. Application Data

(60) Provisional application No. 60/423,590, filed on Nov. 4, 2002.

(30) Foreign Application Priority Data

Jun. 28, 2002 (DE) .......................................... 102 29 180

(51) Int. Cl.$^7$ .............................................. A61K 31/55
(52) U.S. Cl. ................................................ 514/212.05
(58) Field of Search .................................... 514/212.05

(56) References Cited

U.S. PATENT DOCUMENTS

| | | | |
|---|---|---|---|
| 5,430,145 A | 7/1995 | Flynn et al. | |
| 5,484,783 A | 1/1996 | Flynn et al. | |
| 5,624,921 A | 4/1997 | Flynn et al. | |
| 2003/0040509 A1 * | 2/2003 | Moskowitz | 514/171 |

FOREIGN PATENT DOCUMENTS

| | | |
|---|---|---|
| EP | 0481522 | 12/1997 |
| WO | WO 01/15674 | 3/2001 |
| WO | WO 02/083671 | 10/2002 |

OTHER PUBLICATIONS

Hofmann et al, RAGE Mediates a Novel Proinflammatory Axis: A Central Cell Surface Receptor for S100/Calgranulin Polypeptides, Cell., vol. 97, 1999, pp 889–901.

Bralet J et al., Vasopeptidase Inhibitors: an emerging class of cardiovascular drugs, TRENDS in Pharmacological Sciences, 22 (3), Mar. 2001, pp 106–109.

Kilhovd B et al., The ACE Inhibitor ramipril influences the serum levels of advanced glycation endproducts in high risk patients with coronary artery disease: results from a HOPE substudy, The European Society of Cardiology–XXII Congress, Sep. 1–5, 2001, Stockholm, Sweden, abstract 243.

Lewis Edmund J et al., The Effect of Angiotensin–Converting–Enzyme Inhibition on Diabetic Nephropathy, N. England J. Med., 329, 1993, pp 1456–1462.

Molinaro Giuseppe et al., Vasopeptidase inhibitors: a new class of dual zinc metallopeptidase inhibitors for cardiorenal therapeutics, Curr. Opin. Pharmacol., 2002, 2, pp 131–141.

Singh R et al., Advanced glycation end–products: a review, Diabetologia, 44, 2001, pp 129–146.

* cited by examiner

Primary Examiner—Raymond J. Henley III
(74) Attorney, Agent, or Firm—Lawrence L. Martin; Balaram Gupta

(57) ABSTRACT

The invention describes and claims the use of vasopeptidase inhibitors of formula (I)

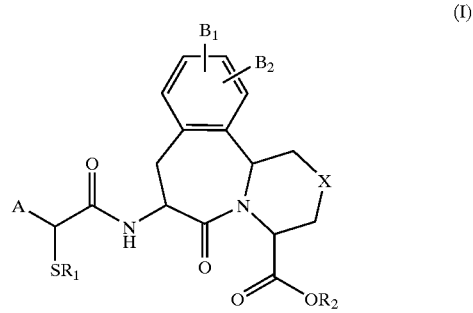

for the treatment of nephropathy in diabetic or non-diabetic patients, including diabetic or non-diabetic nephropathy, glomerulonephritis, glomerular sclerosis, nephrotic syndome, hypertensive nephrosclerosis, microalbuminuria or end stage renal disease, or insulin resistance or of metabolic diseases associated with advanced glycation end-products, such as diabetic complications, diabetic neuropathy, diabetic nephropathy, diabetic retinopathy, cataracts, myocardial infarction and/or diabetic cardiomyopathy, or atherosclerosis or endothelial dysfunction.

15 Claims, 1 Drawing Sheet

USE OF VASOPEPTIDASE INHIBITORS IN THE TREATMENT OF METABOLIC DISEASES, NEPHROPATHY AND ADVANCED GLYCATION END-PRODUCT ASSOCIATED DISEASES

CROSS-REFERENCE TO RELATED APPLICATIONS

This application claims the benefit of priority of German Patent Application No. 10229180.2-41, filed Jun. 28, 2002, and the benefit of U.S. Provisional Application No. 60/423,590, filed Nov. 4, 2002.

BACKGROUND OF THE INVENTION

1. Field of the Invention

The present invention is directed to the use of compounds possessing both angiotensin converting enzyme and neutral endopeptidase inhibitory activity (and classified in the art as vasopeptidase inhibitors) for the treatment of nephropathy in diabetic or non-diabetic patients, including diabetic and non-diabetic nephropathy, glomerulonephritis, glomerular sclerosis, nephrotic syndome, hypertensive nephrosclerosis, microalbuminuria or end stage renal disease, or to a method of treatment and/or prophylaxis of insulin resistance or of metabolic diseases associated with advanced glycation end-products, diabetic complications such as diabetic neuropathy, diabetic nephropathy, diabetic retinopathy, cataracts, myocardial infarction and/or diabetic cardiomyopathy, or to a method of treatment and/or prophylaxis of atherosclerosis or endothelial dysfunction.

2. Description of the Art

Angiotensin-Converting Enzyme (ACE) is a peptidyl dipeptidase which catalyzes the conversion of angiotensin I to angiotensin II. Angiotensin II is a vasoconstrictor which also stimulates aldosterone secretion by the adrenal cortex. ACE inhibition prevents both the conversion of angiotensin I to angiotensin II and the metabolism of bradykinin, resulting in decreased circulating angiotensin II, aldosterone and increased circulating bradykinin concentrations. In addition to these neurohormonal changes, decreases in peripheral resistance and blood pressure are observed, particularly in individuals with high circulating renin. Other pharmacological effects associated with ACE inhibition include regression of left ventricular hypertrophy, improvement in the clinical signs of heart failure, and reduction in mortality in patients with congestive heart failure (CHF) or left ventricular dysfunction after myocardial infarction.

Neutral endopeptidase (NEP) is an enzyme responsible for the metabolism of atrial natriuretic peptide (ANP). Inhibition of NEP results in increased ANP concentrations, which in turn leads to natriuresis, diuresis and decreases in intravascular volume, venous return and blood pressure. ANP is released by atrial myocytes in response to atrial stretch or increased intravascular volume. Elevated plasma concentrations of ANP have been demonstrated as a potential compensatory mechanism in various disease states, including congestive heart failure, renal failure, essential hypertension and cirrhosis.

The secretion of ANP by atrial myocytes causes vasodilation, diuresis, natriuresis, and the inhibition of renin release and aldosterone secretion. In contrast, angiotensin II results in vasoconstriction, sodium and water reabsorption, and aldosterone production. These two hormonal systems interact in a reciprocal or counterbalancing manner to maintain normal physiologic vascular and hemodynamic responses.

U.S. Pat. No. 5,430,145, European patent EP 481522 and WO patent application PCT/EP 02/03668 disclose tricyclic mercaptoacetylamide derivatives of formula (I) useful as ACE and NEP inhibitors, i.e. for the treatment and/or prevention of heart failure and hypertension. Compounds that inhibit both angiotensin-converting enzyme and neutral endopeptidase are classified as "vasopeptidase inhibitors" (VPIs), and act to both reduce the activity of the renin-angiotensin system and to potentiate the vasodilatory, natriuretic and antiproliferative effects of bradykinin and natriuretic peptides. In preclinical studies, VPIs display a broad profile being effective in all tested models of hypertension and heart failure, and ongoing clinical studies suggest that VPIs possess advantages over other therapies (Jean Bralet and Jean-Charles Schwartz, TRENDS in Pharmacological Sciences, 22 (3), 106–109 (2001)).

SUMMARY OF THE INVENTION

This invention is directed to the use of a compound of formula (I)

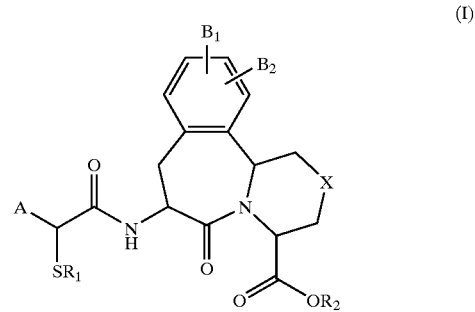

wherein
A is H, $C_1$–$C_8$-alkyl, —$CH_2OCH_2CH_2OCH_3$, or —($C_1$–$C_4$-alkyl)-aryl;
$R_1$ is hydrogen, —$CH_2OC(O)C(CH_3)_3$, or an acyl group;
$R_2$ is hydrogen; —$CH_2OC(O)C(CH_3)_3$; —$C_1$–$C_4$-alkyl; aryl, —($C_1$–$C_4$-alkyl)-aryl; or diphenylmethyl;
X is —$(CH_2)_n$ wherein n is an integer 0 or 1, —S—, —O—,

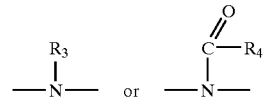

wherein $R_3$ is hydrogen, $C_1$–$C_4$-alkyl, aryl or —($C_1$–$C_4$-alkyl)-aryl; and $R_4$ is —$CF_3$, $C_1$–$C_{10}$-alkyl, aryl, or —($C_1$–$C_4$-alkyl)-aryl;
$B_1$ and $B_2$ are each independently hydrogen, hydroxy, —$OR_5$, wherein $R_5$ is $C_1$–$C_4$-alkyl, aryl, or —($C_1$–$C_4$-alkyl)-aryl or, where $B_1$ and $B_2$ are attached to adjacent carbon atoms, $B_1$ and $B_2$ can be taken together with said adjacent carbon atoms to form a benzene ring or methylenedioxy,
for the treatment and/or prophylaxis of nephropathy in diabetic or non-diabetic patients, including diabetic and non-diabetic nephropathy, glomerulonephritis, glomerular sclerosis, nephrotic syndome, hypertensive nephrosclerosis, microalbuminuria or end stage renal disease, or to a method of treatment and/or prophylaxis of insulin resistance or of metabolic diseases associated with advanced glycation end-products, diabetic complications such as diabetic neuropathy, diabetic nephropathy, diabetic retinopathy, cataracts, myocardial infarction and/or diabetic cardiomyopathy, or to a method of treatment and/or prophylaxis of atherosclerosis or endothelial dysfunction.

In one embodiment, the present invention provides the above uses of a compound of a formula (I) characterized by a compound of formula (II)

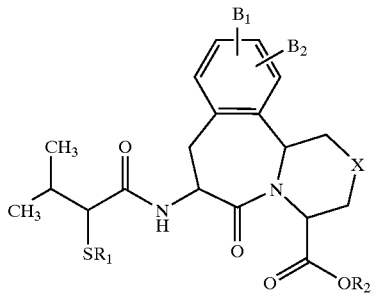

(II)

wherein $R_1$ is acetyl. In another embodiment, the present invention provides the above uses of a compound of the formula (II) wherein $R_1$ is hydrogen. In a further embodiment, the present invention provides the above uses of a compound of the formula (II) wherein $R_2$ is hydrogen. In a further embodiment, the present invention provides the above uses of a compound of the formula (II) wherein $B_1$ and/or $B_2$ are hydrogen. In yet a further embodiment, the present invention provides the above uses of a compound of the formula (II) wherein X is —$CH_2$.

In a further embodiment, the present invention provides the above uses of a compound of formula (I) characterized by a compound of formula (II-A)

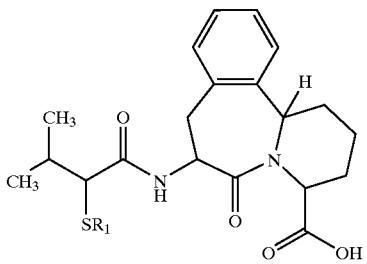

(II-A)

wherein $R_1$ is acetyl or hydrogen.

The structure of preferred compounds of formulae (II-A) are the compound of formula (II-B), also referred to as compound (II-B) or cpd. (II-B), and the compound of formula (II-C) below:

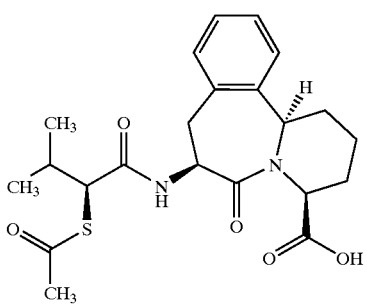

(II-B)

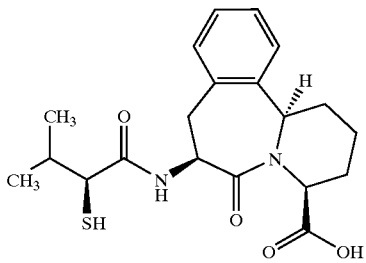

(II-C)

In a further embodiment, the present invention provides the above uses of a compound of formula (I) characterized by a compound of formula (III)

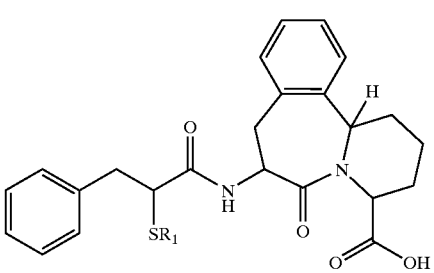

(III)

wherein $R_1$ is acetyl. In another embodiment, the present invention provides the above uses of a compound of formula (III) wherein $R_1$ is hydrogen. In a further embodiment, the present invention provides the above uses of a compound of formula (III) wherein $R_2$ is hydrogen. In a further embodiment, the present invention provides the above uses of a compound of formula (III) wherein $B_1$ and/or $B_2$ are hydrogen. In yet a further embodiment, the present invention provides the above uses of a compound of formula (III) wherein X is —$CH_2$.

In a further embodiment, the present invention provides the above uses of a compound of formula (I) characterized by a compound of formula (III-A):

(III-A)

wherein $R_1$ is acetyl or hydrogen.

The structure of preferred compounds of formulae (III-A) are of formulae (III-B) and (III-C) below:

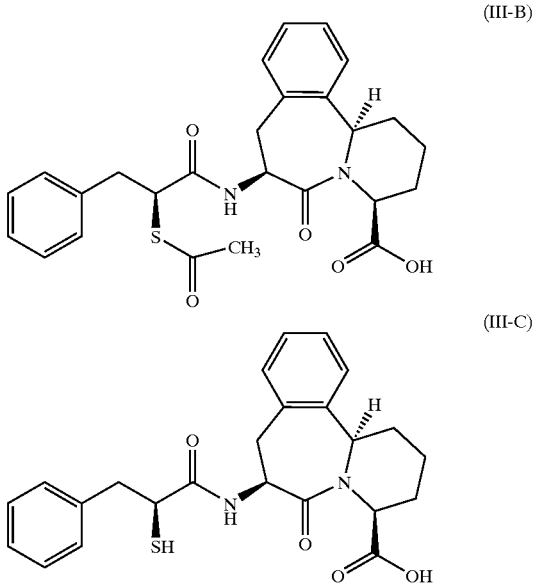

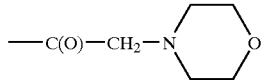

DETAILED DESCRIPTION OF THE INVENTION

Figure 1:
FIG. 1 shows Advanced Glycation End-product (AGE) related non-diabetic nephropathy in placebo-treated Wistar rats (kidney of a placebo rat displaying moderate tubulo-interstitial lesions (proteinaceous casts in the tubules, inflammatory cell infiltration, basophilic tubules)); orig. magn. ×100.

As used herein, the term '$C_1$–$C_4$-alkyl' refers to a saturated straight or branched monovalent hydrocarbon chain of one, two, three or four carbon atoms and includes methyl, ethyl, propyl, isopropyl, n-butyl, isobutyl, tertiary butyl, and the like groups. The term '$C_1$–$C_{10}$-alkyl' refers to a saturated straight or branched monovalent hydrocarbon chain of one to ten carbon atoms and includes methyl, ethyl, propyl, isopropyl, n-butyl, isobutyl, tertiary butyl, pentyl, isopentyl, hexyl, 2,3-dimethyl-2-butyl, heptyl, 2,2-dimethyl-3-pentyl, 2-methyl-2-hexyl, octyl, 4-methyl-3-heptyl and the like groups.

As used herein, '$C_1$–$C_4$-alkoxy' refers to a monovalent substituent which consists of a straight or branched alkyl chain having from 1 to 4 carbon atoms linked through an ether oxygen atom and having its free valence bond from the ether oxygen, and includes methoxy, ethoxy, propoxy, isopropoxy, butoxy, sec-butoxy, tert-butoxy and the like groups.

As used herein, 'aryl' refers to a phenyl or naphthyl group unsubstituted or substituted with from one to three substituents selected from the group consisting of methylenedioxy, hydroxy, $C_1$–$C_4$-alkoxy, fluoro and chloro. Included within the scope of the term '—($C_1$–$C_4$-alkyl)-aryl' are phenylmethyl (benzyl), phenylethyl, p-methoxybenzyl, p-fluorobenzyl and p-chlorobenzyl.

As used herein, 'halogen' or 'Hal' refers to a member of the family of fluorine, chlorine, bromine or iodine.

As used herein, 'acyl group' refers to aliphatic and aromatic acyl groups and those derived from heterocyclic compounds. For example, the acyl group may be a lower or ($C_1$–$C_4$)alkanoyl group such as formyl or acetyl, an aroyl group such as benzoyl or a heterocyclic acyl group comprising one or more of the heteroatoms O, N and S, such as the group As used herein, 'stereoisomer' is a general term used for all isomers of individual molecules that differ only in the orientation of their atoms in space. The term stereoisomer includes mirror image isomers (enantiomers), geometric (cis/trans or E/Z) isomers, and isomers of compounds with more than one chiral center that are not mirror images of one another (diastereoisomers).

As used herein, 'R' and 'S' are used as commonly used in organic chemistry to denote specific configuration of a chiral center. The term 'R' (rectus) refers to that configuration of a chiral center with a clockwise relationship of group priorities (highest to second lowest) when viewed along the bond toward the lowest priority group. The term 'S' (sinister) refers to that configuration of a chiral center with a counter clockwise relationship of group priorities (highest to second lowest) when viewed along the bond toward the lowest priority group. The priority of groups is based upon sequence rules wherein prioritization is first based on atomic number (in order of decreasing atomic number). A listing and discussion of priorities is contained in Stereochemistry of Organic Compounds, Ernest L. Eliel, Samuel H. Wilen and Lewis N. Mander, editors, Wiley-Interscience, John Wiley & Sons, Inc., New York, 1994.

In addition to the (R)-(S) system, the older D-L system may also be used herein to denote absolute configuration, especially with reference to amino acids. In this system a Fischer projection formula is oriented so that the number 1 carbon of the main chain is at the top. The prefix 'D' is used to represent the absolute configuration of the isomer in which the functional (determining) group is on the right side of the carbon at the chiral center and 'L', that of the isomer in which it is on the left.

As used herein, 'treat' or 'treating' means any treatment, including but not limited to, alleviating symptoms, eliminating the causation of the symptoms either on a temporary or permanent basis, or to preventing or slowing the appearance of symptoms and progression of the named disease, disorder or condition.

As described herein, the term 'patient' refers to a warm blooded animal such as a mammal which is afflicted with a particular disease, disorder or condition. It is explicitly understood that guinea pigs, dogs, cats, rats, mice, horses, cattle, sheep, and humans are examples of animals within the scope of the meaning of the term.

As used herein, the term 'pharmaceutically acceptable salt' is intended to apply to any salt, whether previously known or future discovered, that is used by one skilled in the art that is a non-toxic organic or inorganic addition salt which is suitable for use as a pharmaceutical. Illustrative bases which form suitable salts include alkali metal or alkaline-earth metal hydroxides such as sodium, potassium, calcium or magnesium hydroxides; ammonia and aliphatic, cyclic or aromatic amines such as methylamine, dimethylamine, triethylamine, diethylamine, isopropyldiethylamine, pyridine and picoline. Illustrative acids which form suitable salts include inorganic acids such as, for example, hydrochloric, hydrobromic, sulfuric, phosphoric and like acids, and organic carboxylic acids such as, for example, acetic, propionic, glycolic, lactic, pyruvic, malonic, succinic, fumaric, malic, tartaric, citric, ascorbic, maleic, hydroxymaleic and dihydroxymaleic, benzoic, phenylacetic, 4-aminobenzoic, 4-hydroxybenzoic, anthranilic, cinnamic, salicylic, 4-aminosalicylic, 2-phenoxybenzoic, 2-acetoxybenzoic, mandelic and like acids, and organic sulfonic acids such as methanesulfonic and p-toluenesulfonic acids.

As used herein, 'pharmaceutical carrier' refers to known pharmaceutical excipients useful in formulating pharmaceutically active compounds for administration, and which are substantially nontoxic and non-sensitizing under conditions of use. The exact proportion of these excipients is determined by the solubility and chemical properties of the active compound, the chosen route of administration as well as standard pharmaceutical practice.

The compositions of the compound of formula (I) of this invention may be administered to a subject in need of treatment by a variety of conventional routes of administration, including orally, topically, parenterally, e.g., intravenously, subcutaneously or intramedullary. Further, the active compositions of this invention may be administered intranasally, as a rectal suppository, or orally using a "flash" formulation, i.e., allowing the medication to dissolve in the mouth without the need to use water.

The active compositions of this invention may be administered alone or in combination with pharmaceutically acceptable carriers, vehicles or diluents, in either single or multiple doses. Suitable pharmaceutical carriers, vehicles and diluents include inert solid diluents or fillers, sterile aqueous solutions and various organic solvents. The pharmaceutical compositions formed by combining the active compositions of this invention and the pharmaceutically acceptable carriers, vehicles or diluents are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerol and combinations thereof.

For parenteral administration, solutions of the active compositions of this invention in sesame or peanut oil, aqueous propylene glycol, or in sterile aqueous solutions may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, the sterile aqueous media employed are all readily available by standard techniques known to those skilled in the art.

Generally, a composition of this invention is administered orally, parenterally (e.g., intravenous, intramuscular, subcutaneous or intramedullary), or topically. For intranasal administration or administration by inhalation, one or more compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch. For purposes of transdermal (e.g., topical) administration, dilute sterile, aqueous or partially aqueous solutions (usually in about 0.1% to 5% concentration), otherwise similar to the above parenteral solutions, are prepared.

Methods of preparing various pharmaceutical compositions with a certain amount of active ingredient are known, or will be apparent in light of this disclosure, to those skilled in this art. For examples of methods of preparing pharmaceutical compositions, see Remington's Pharmaceutical Sciences, Mack Publishing Company, Easton, Pa., 19th Edition (1995).

Nephropathy

Nephropathy is a chronic disease that is defined as abnormality in the excretion of urinary albumin in diabetic or non-diabetic patients. Urinary albumin excretion rates are less than or equal to 40 mg/24 hours in healthy humans. The clinical stages of nephropathy are microalbuminuria, clinical nephropathy (albuminuria) and end-stage renal disease (ESRD).

A common form of nephropathy is diabetic nephropathy. Diabetic nephropathy develops in 35 to 40% of patients with type 1 diabetes mellitus and in 10 to 60% of patients with type 2 diabetes mellitus depending upon the ethnic pool being studied and is the most common cause of end-stage renal disease in the United States. It is accepted that diabetic nephropathy is the result of hyperglycemia, whether alone or in combination with other factors, such as hypertension and genetic susceptibility to kidney disease. Appropriate antihypertensive therapy has been shown to significantly reduce renal and possibly cardiovascular mortality in proteinuric type 1 diabetes mellitus patients, as well as retard the rate of decline of glomerular filtration rate in some patients with impaired renal function (Lewis et al., N. Engl. J. Med. 1993, 329, 1456–1462). Thus, the standard care for patients with diabetic nephropathy is intensive glycemic control and normalization of the blood pressure using primarily angiotensin converting enzyme (ACE) inhibitors such as ramipril.

Some vasopeptidase inhibitors have been shown to exhibit a greater nephroprotective effect than ACE inhibitors alone (Molinaro et al., Curr. Opin. Pharmacol. 2002, 2, 131–141), such as omapatrilat as one of the earliest developed and the most extensively evaluated vasopeptidase inhibitors. Chen et al. (Hypertension 2001, 38, 187–191) defined the renal action of acute treatment with omapatrilat and ACE inhibitor fosinoprilat, wherein omapatrilat had a greater natriuretic response than the ACE inhibitor. In another study, vasopeptidase inhibitor CGS 30440 (Novartis, Switzerland) had a greater renal protective effect than ACE inhibitor benazepril (Cohen et al., J. Cardiovasc. Pharmacol. 1998, 32, 87–95).

It has now been shown that vasopeptidase inhibitors of formula (I) have a superior nephroprotective effect in albumin excretion rate and are therefore useful for the treatment and/or prevention of nephropathy in diabetic and non-diabetic patients, including diabetic nephropathy, glomerulonephritis, glomerular sclerosis, nephrotic syndrome, hypertensive nephrosclerosis, microalbuminuria and end stage renal disease.

EXPERIMENTAL

The effect of compound (II-B) is 6–8 fold higher than observed with the ACE inhibitor ramipril.

Example 1

Diminishing Proteinuria by Treatment with a Compound of Formula (II-B)

The protein and creatinine excretion in the urine of male Zucker Diabetic Fatty (ZDF) Rats (ZDF Gmi fa/fa) and heterozygous control animals (ZDF Gmi −/+) of 10, 17, 27 and 37 weeks age was determined. In further groups, diabetic rats were chronically given either ramipril (1 mg/kg/day, in drinking water) or a compound of formula (II-B) (30 mg/kg/day, in food) over a period from 10 to 37 weeks. The animals were sacrificied after 37 weeks, and their kidneys examined histologically.

Histological Results

In the attached tables a summary of the findings on the kidneys after a treatment period of 6 months is listed. The examined groups were:

| C1: | Control | lean ZDF rats | |
| C2: | Control | fat ZDF rats | |
| D1: | ramipril | fat ZDF rats | 1.0 mg/kg |
| D4: | cpd. (II-B) | fat ZDF rats | 30 mg/kg |

Histopathological findings noted were:

| Armanni-Ebstein cells | in renal tubules indicating a diabetic metabolic state. |
| Glomerulosclerosis | indicating chronic kidney damage due to a diabetic metabolic state. |
| Atrophy: tubule | common spontaneous degenerative lesion in kidneys. |
| Casts: tubule | common spontaneous lesion in kidneys. |
| Dilatation: pelvis | common spontaneous lesion in kidneys. considered to be an inherited developmental anomaly. |

Armanni-Ebstein cells were not present in lean ZDF control rats but were found in every group of treated fat ZDF rats (groups D1 and D4). Glomerulosclerosis was not found in lean ZDF control rats and was also not present in animals

TABLE 1

Urinary excretion of albumin and creatinine in ZDF rats, lean ZDF rats, ramipril-treated ZDF rats and ZDF rats treated with the compound of formula (II-B)

| Urine excretion | Albumin mg/kg/h | | | | Albumin/Creatinine mg/mmol | | | |
| --- | --- | --- | --- | --- | --- | --- | --- | --- |
| Weeks | 0 | 7 | 17 | 27 | 0 | 7 | 17 | 27 |
| Group 1 Obese | | | | | | | | |
| Mean | 0.35 | 1.78 | 9.24 | 14.23 | 55.27 | 404.78 | 975.60 | 1543.25 |
| s | 0.24 | 1.09 | 6.70 | 7.69 | 41.58 | 349.65 | 714.38 | 819.04 |
| SEM | 0.06 | 0.28 | 2.02 | 2.32 | 10.74 | 90.28 | 215.40 | 246.95 |
| N | 15 | 15 | 11 | 11 | 15 | 15 | 11 | 11 |
| Group 2 Lean | | | | | | | | |
| Mean | 0.121 | 0.090 | 0.070 | 0.079 | 12.828 | 9.573 | 5.754 | 7.313 |
| s | 0.041 | 0.069 | 0.033 | 0.051 | 4.206 | 6.010 | 2.772 | 4.541 |
| SEM | 0.009 | 0.015 | 0.008 | 0.014 | 0.940 | 1.344 | 0.693 | 1.260 |
| N | 20 | 20 | 16 | 13 | 20 | 20 | 16 | 13 |
| t-Test | 0.000 | 0.000 | 0.000 | 0.000 | 0.000 | 0.000 | 0.000 | 0.000 |
| Group 4 ramipril | | | | | | | | |
| Mean | 0.24 | 1.36 | 6.26 | 10.11 | 37.31 | 207.35 | 694.20 | 1077.88 |
| s | 0.12 | 1.28 | 4.71 | 7.20 | 17.20 | 198.42 | 510.20 | 742.86 |
| SEM | 0.03 | 0.33 | 1.42 | 2.17 | 4.44 | 51.23 | 153.83 | 223.98 |
| N | 15 | 15 | 11 | 11 | 15 | 15 | 11 | 11 |
| t-Test | 0.122 | 0.338 | 0.242 | 0.209 | 0.133 | 0.067 | 0.300 | 0.178 |
| Group 7 cpd. (II-B) | | | | | | | | |
| Mean | 0.27 | 0.09 | 0.41 | 1.39 | 48.56 | 14.30 | 44.63 | 152.71 |
| s | 0.18 | 0.04 | 0.18 | 1.67 | 28.69 | 5.38 | 16.47 | 174.93 |
| SEM | 0.05 | 0.01 | 0.05 | 0.50 | 7.41 | 1.39 | 4.97 | 52.74 |
| N | 15 | 15 | 11 | 11 | 15 | 15 | 11 | 11 |
| t-Test | 0.293 | 0.000 | 0.000 | 0.000 | 0.611 | 0.000 | 0.000 | 0.000 | treated with compound (II-B). Correspondingly, degenerative lesions, atrophy of tubules and tubular casts were found in low incidences in these animals. Compared to fat ZDF controls, in ramipril or compound (III-B) (MDL 100,240) treated rats no differences in the incidence of glomerulosclerosis or associated degenerative lesions was present.

These results indicate that treatment with compound (III-B) may prevent the development of "diabetic" glomerulosclerosis and associated degenerative lesions. The lesions in the fat ZDF control rats were of rather low severity. In addition, a high incidence of pelvic dilatation was noted in animals treated with compound (II-B).

Explanation of Codes and Symbols

Codes and Symbols Used at Animal Level:

KO=Terminal sacrifice group

TABLE 2

Histological findings:

| SEX | Males | | | |
|---|---|---|---|---|
| Dose Group | C1 | C2 | D1 | D4 |
| NUMBER OF ANIMALS WITH MICROSCOPIC FINDINGS BY ORGAN/GROUP/SEX Necropsy status: TERMINAL SACRIFICE GROUP (KO) | | | | |
| No. Animals per Dose Group | 12 | 6 | 9 | 9 |
| Kidneys No. Examined | 12 | 6 | 9 | 8 |
| Armanni-Ebstein cells | — | 6 | 7 | 8 |
| Glomerulosclerosis | — | 6 | 6 | 1 |
| Atrophy: renal tubule | — | 6 | 9 | 2 |
| Casts: renal tubule | 1 | 6 | 8 | 3 |
| Dilatation: pelvis | 3 | 2 | 5 | 7 |
| SUMMARY INCIDENCE OF GRADINGS BY ORGAN/GROUP/SEX Necropsy Status: TERMINAL SARCRIFICE GROUP (KO) | | | | |
| No. Animals per Dose Group | 12 | 6 | 9 | 9 |
| Kidneys No. Examined | 12 | 6 | 9 | 8 |
| Armanni-Ebstein cells GRADE 1 | — | 2 | 1 | — |
| GRADE 2 | — | 3 | 6 | 5 |
| GRADE 3 | — | 1 | — | 3 |
| TOTAL AFFECTED | — | 6 | 7 | 8 |
| MEAN SEVERITY | — | 1.8 | 1.9 | 2.4 |
| Glomerulosclerosis GRADE 1 | — | 1 | — | 1 |
| GRADE 2 | — | 3 | 4 | — |
| GRADE 3 | — | 2 | 2 | 1 |
| TOTAL AFFECTED | — | 6 | 6 | 1 |
| MEAN SEVERITY | — | 2.2 | 2.3 | 1.0 |
| Atrophy: renal tubule GRADE 1 | — | 2 | 4 | 1 |
| GRADE 2 | — | 2 | 4 | — |
| GRADE 3 | — | 1 | 1 | 1 |
| GRADE 4 | — | 1 | — | — |
| TOTAL AFFECTED | — | 6 | 9 | 2 |
| MEAN SEVERITY | — | 2.2 | 1.7 | 2.0 |
| Casts: renal tubule GRADE 1 | 1 | 1 | 1 | 2 |
| GRADE 2 | — | 4 | 7 | 1 |
| GRADE 3 | — | 1 | — | — |
| TOTAL AFFECTED | 1 | 6 | 8 | 3 |
| MEAN SEVERITY | 1.0 | 2.0 | 1.9 | 1.3 |
| Dilatation: pelvis GRADE 2 | 3 | — | 1 | 1 |
| GRADE 3 | — | 1 | 2 | 5 |
| GRADE 4 | — | 1 | 2 | 1 |
| TOTAL AFFECTED | 3 | 2 | 5 | 7 |
| MEAN SEVERITY | 2.0 | 3.5 | 3.2 | 3.0 |

TABLE 3

Urinary excretion of albumin and creatinine in ZDF rats, ramipril-treated ZDF rats and ZDF rats treated with the compound of formula (II-B) starting at an animal age of 6 months.
ZDF rats are a model for Type II diabetes.

| | Albumin/Creatinine mg/mmol | | |
|---|---|---|---|
| | Basal | 6 weeks treatment | 12 weeks treatment |
| Placebo ZDF rats | | | |
| mean | 1330.99 | 1068.25 | 1193.47 |
| s | 797.55 | 778.81 | 633.10 |
| SEM | 230.23 | 224.82 | 182.76 |
| N | 12 | 12 | 12 |
| Cpd. (II-B) ZDF rats | | | |
| Mean | 1330.99 | 135.08 | 100.86 |
| S | 797.55 | 40.28 | 59.27 |
| SEM | 230.23 | 11.63 | 17.11 |
| N | 12 | 12 | 12 |
| ramipril ZDF rats | | | |
| Mean | 1330.99 | 1249.59 | 841.69 |
| S | 797.55 | 1036.03 | 1124.24 |
| SEM | 230.23 | 299.07 | 324.54 |
| N | 12 | 12 | 12 |

Example 2

The albumin and creatinine excretion in Goto-Kakizaki (GK) rats was determined. GK rats are a model for Type II diabetes. One group was left untreated, one was treated with the ACE/NEP inhibitor of formula (II-B) and one group was treated with the ACE inhibitor ramipril.

TABLE 4

Urinary excretion of albumin and creatinine in GK rats, ramipril-treated GK rats and GK rats treated with the compound of formula (II-B) starting at an animal age of 6 months

| | Albumin/Creatinine mg/mmol | | |
|---|---|---|---|
| | Basal | 6 weeks treatment | 12 weeks treatment |
| Placebo GK rats | | | |
| Mean | 103.95 | 329.37 | 1183.19 |
| s | 71.42 | 230.17 | 637.71 |
| SEM | 20.62 | 66.44 | 184.09 |
| N | 12 | 12 | 12 |
| Cpd. (II-B) GK rats | | | |
| Mean | 103.95 | 17.70 | 24.28 |
| s | 71.42 | 6.01 | 14.41 |
| SEM | 20.62 | 1.74 | 4.16 |
| N | 12 | 12 | 12 |

TABLE 4-continued

Urinary excretion of albumin and creatinine in GK rats,
ramipril-treated GK rats and GK rats treated with the
compound of formula (II-B) starting at an animal age
of 6 months

| | | Albumin/Creatinine mg/mmol | |
|---|---|---|---|
| | Basal | 6 weeks treatment | 12 weeks treatment |
| ramipril GK rats | | | |
| Mean | 103.95 | 161.71 | 244.89 |
| S | 71.42 | 112.42 | 146.00 |
| SEM | 20.62 | 32.5 | 44.0 |
| N | 12 | 12 | 11 |

Example 3

The albumin and creatinine excretion in Wistar rats was determined. One group was left untreated, one was treated with the ACE/NEP inhibitor of formula (II-B) and one group was treated with the ACE inhibitor ramipril. Wistar rats are non-diabetic and develop proteinuria and structural kidney damage during adult life. Wistar rats are therefore a model for non-diabetic nephropathy.

FIG. 1 shows AGE-related non-diabetic nephropathy in placebo-treated Wistar rats (kidney of a placebo rat displaying moderate tubulo-interstitial lesions (proteinaceous casts in the tubules, inflammatory cell infiltration, basophilic tubules)).

TABLE 5

Urinary excretion of albumin and creatinine in Wistar rats,
ramipril-treated Wistar rats and Wistar rats treated with
the compound of formula (II-B) starting at an animal age
of 6 months

| | | Albumin/Creatinine mg/mmol | |
|---|---|---|---|
| | Basal | 6 weeks treatment | 12 weeks treatment |
| Placebo Wistar rats | | | |
| Mean | 130.45 | 149.82 | 290.10 |
| S | 285.53 | 231.12 | 265.69 |
| SEM | 90.29 | 64.10 | 73.69 |
| N | 10 | 13 | 13 |
| Cpd. (II-B) Wistar rats | | | |
| Mean | 130.45 | 18.07 | 21.21 |
| S | 285.53 | 17.64 | 29.49 |
| SEM | 90.29 | 4.89 | 8.18 |
| N | 10 | 13 | 13 |
| ramipril Wistar rats | | | |
| Mean | 130.45 | 184.27 | 188.40 |
| S | 285.53 | 171.87 | 146.47 |
| SEM | 90.29 | 49.62 | 42.28 |
| N | 10 | 12 | 12 |

In the non-diabetic model, the compound of formula (II-B) shows a significantly higher nephroprotective effect than ramipril as determined by the extent of proteinuria.

Advanced Glycation End-product Related Diseases

Incubation of proteins or lipids with aldose sugars results in nonenzymatic glycation and oxidation of amino groups on proteins to form Amadori adducts. Over time, the adducts undergo additional rearrangements, dehydrations, and cross-linking with other proteins to form complexes known as Advanced Glycation End-Products (AGEs). The formation of AGEs can also be described as Maillard reactions. Factors which promote formation of AGEs include delayed protein turnover (e.g. as in amyloidoses), accumulation of macromolecules having high lysine content, and high blood glucose levels (e.g. as in diabetes) (Hori et al., J. Biol. Chem. 270: 25752–761, (1995)). AGEs have been implicated in a variety of disorders including complications associated with diabetes and normal aging.

AGEs display specific and saturable binding to cell surface receptors on endothelial cells of the microvasculature, monocytes and macrophages, smooth muscle cells, mesengial cells, and neurons. The Receptor for Advanced Glycated End-Products (RAGE) is a member of the immunoglobulin super family of cell surface molecules.

Increased levels of RAGE are found in aging tissues (Schleicher et al., J. Clin. Invest. 1997, 99, 457–468), and the diabetic retina, vasculature and kidney (Schmidt et al., Nature Med. 1995, 1002–1004). Activation of RAGE in different tissues and organs leads to a number of pathophysiological consequences. RAGE has been implicated in a variety of conditions including: acute and chronic inflammation (Hofmann et al, Cell 1999, 97, 889–901), the development of diabetic late complications such as increased vascular permeability, nephropathy, atherosclerosis, and retinopathy by accumulation of AGEs in the kidneys and other tissues (Singh et al., Diabetologia 2001, 44, 129–146), as well as in Alzheimer's disease (Yan et al., Nature 1996, 382, 685–691), erectile dysfunction, tumor invasion and metastasis (Taguchi et al., Nature 2000, 405, 354–357).

The ACE inhibitor ramipril is known to influence the serum levels of advanced glycation end-products in high risk patients with coronary artery disease: results from a HOPE study (B. Kilhovd, E. M. Hjerkinn, I. Seljeflot, T. J. Berg, and A. Reikvam, The European Society of Cardiology—XXIII Congress, Sep. 1–5, 2001, Stockholm, Sweden, abstract 243).

It has now been found that compounds of formula (I) significantly reduce the accumulation of AGEs in the kidneys and in the heart. Therefore, compounds of formula (I) are useful for the prevention and/or treatment of metabolic diseases associated with advanced glycation end-products, especially diabetic complications such as diabetic neuropathy, diabetic nephropathy, diabetic retinopathy, myocardial infarction, cataracts and diabetic cardiomyopathy.

Kidney AGE values were determined by Dot blot analysis (Stracke et al., Exp. Clin. Endocrinol. Diabets 2002, 109, 330–336) and Reversed-phase high performance liquid chromatography or RP-HPLC (Drusch et al., Food Chem. 1999, 65, 547–553).

Treatment of diabetic rats with the compound of formula (II-B) normalizes the kidney AGE (Nε-(carboxymethyl) lysine or CML) values, treatment with the compound of formula (III-B) (MDL 100,240 or M100,240) lowers the CML value significantly.

Example 4

Dot Blot Analysis

Kidney-samples for the dot blot analysis were obtained from 17-week-old male ZDF rats, control rats and ZDF rats treated for seven weeks with 30 mg/kg/d of compound (II-B) and 35 mg/kg/d of compound (III-B). Three animals of each group were sacrificed, the kidneys removed and immediately frozen in liquid nitrogen. Grinding of the kidneys was performed in liquid nitrogen using a freezer mill (Freezer 6750, C3 Analysetechnik GmbH). Kidney sample (10 mg) was dissolved in 1 ml phosphate buffered saline (PBS containing 0.5 g/l Tween 20, 0.5 mM PMSF, 1 µg/ml). The solution was treated two times for five seconds with an ultrasonic cell disrupter (45% power, Bandolin Sonoplus HD 2070), centrifuged for 20 minutes at 4000 rpm and the supernatant was used for dot blot analysis. The nitrocellulose membrane was placed in the dot blot apparatus and washed twice with Tris Buffered Saline (TBS), 100 µl TBS/well. For each sample, 10 µg protein (protein concentration of the samples were determined with the DC Protein Assay, Bio Rad) was diluted in 100 µl TBS and loaded on to the nitrocellulose membrane (Amersham). The membrane was incubated over night in TBS with Tween 20 (TBST; 20 mM Tris, 137 mM NaCl, 0.05% v/v Tween 20) with 5% non-fat dry milk at 4° C. and incubated for 1 hour at room temperature using the following antibody concentration: anti-CML 011 (Biologo) 0.25 µg/ml, anti-CEL (Biologo) 0.25 µg/ml and anti-pentosidine 012 (Biologo) 0.25 µg/ml. After extensive washing in TBST with 5% non-fat dry milk, membranes were exposed to alkaline peroxidase-labeled anti-mouse IgG antibodies (Dianova) for one hour at room temperature. Membranes were washed again and exposed to the enhanced chemofluorescence detection system (Amersham) according to manufacturer's instructions. Relative fluorescence was determined with the Fluor-Imager 595 (Molecular Dynamics) and quantified using the Image-Quant software. Results were expressed in relative fluorescence (rf) times $10^5$ (rf*$10^5$).

TABLE 6

Values of the AGE-subtype CML in the kidneys of 17-week-old ZDF rats, control rats and ZDF rats treated with compound (II-B) or with compound (III-B). Values with P < 0.05 were considered significant (*P < 0.05)

| kidneys of 17 week old rats anti-CML 011 | n | mean rf * $10^5$ | SEM rf * $10^5$ | t-test | sign. |
|---|---|---|---|---|---|
| Lean control | 3 | 32.20 | 1.22 | | |
| ZDF rats | 3 | 45.14 | 3.23 | 0.0199 | * |
| ZDF cpd. (II-B) | 3 | 32.62 | 0.34 | 0.0182 | * |
| ZDF cpd. (IIIB) | 3 | 38.67 | 1.38 | 0.1389 | |

TABLE 7

Values of the AGE-subtype CEL in the kidneys of 17-week-old ZDF rats, control rats and ZDF rats treated with compound (II-B) or compound (III-B).

| kidneys of 17 week old rats anti-CEL | n | mean rf * $10^5$ | SEM rf * $10^5$ |
|---|---|---|---|
| Lean control | 3 | 54.49 | 2.55 |
| ZDF rats | 3 | 61.30 | 1.12 |
| ZDF cpd. (II-B) | 3 | 50.24 | 0.46 |
| ZDF cpd. (III-B) | 3 | 52.60 | 1.16 |

TABLE 8

Values of the AGE-subtype pentosidine in the kidneys of 17-week-old ZDF rats, control rats and ZDF rats treated with compound (II-B) or compound (III-B).

| kidneys of 17-week-old rats anti-pentosidine 012 | n | mean rf * $10^5$ | SEM rf * $10^5$ |
|---|---|---|---|
| Lean control | 3 | 52.78 | 1.65 |
| ZDF rats | 3 | 56.01 | 1.24 |
| ZDF cpd. (II-B) | 3 | 44.99 | 1.61 |
| ZDF cpd. (III-B) | 3 | 40.70 | 2.75 |

Values of the AGE-subtype CML are significantly higher in kidneys of ZDF rats compared to the control rats (P<0.05). No significant difference between ZDF and control rats could be shown for the AGE-subtypes CEL and pentosidine. ZDF rats treated with the compound of formula (II-B) show significantly less AGE values for the AGE-subtype CML, CEL and pentosidine (P<0.05) compared to untreated ZDF rats. Lower AGE values for the subtypes CEL and pentosidine can also be determined in ZDF rats treated with compound (III-B) (P<0.01).

Example 5

Reversed-phase High Performance Liquid Chromatography (RP-HPLC)

Kidney- and heart-samples for the RP-HPLC analysis were obtained from 17-week-old male ZDF rats, control rats and ZDF rats treated for seven weeks with 30 mg/kg/d of the compound of formula (II-B) and 35 mg/kg/d of the compound of formula (III-B). Two animals of each group were analyzed. Grinding of the kidney and heart was performed in liquid nitrogen using a freezer mill (Freezer 6750, C3 Analysetechnik GmbH). Hydrolysis of the organ samples was performed with 6 M hydrochloric acid (HCl) at 110° C. for 12 hours. Sample treatment with o-phthaldialdehyde (OPA) and RP-HPLC was performed as described in Drusch et al., Food Chem. 1999, 65, 547–553.

TABLE 9

Values of the AGE-subtypes CML in the kidneys of 17-week-old ZDF rats, control rats and ZDF rats treated with the compound of formula (II-B) or the compound of formula (III-B).

| RP-HPLC kidneys 17 week old rats | n [animals] | mean CML conc. [%] | SEM [%] |
|---|---|---|---|
| ZDF Placebo | 2 | 100 | 0.27 |
| Lean control | 2 | 84 | 1.19 |
| Cpd. (II-B) | 2 | 55 | 3.83 |
| Cpd. (III-B) | 2 | 60 | 10.15 |

TABLE 10

Values of the AGE-subtypes CML in the kidneys of 37-week-old ZDF rats, control rats and ZDF rats treated with the compound of formula (II-B) or the compound of formula (III-B). Values with P < 0.05 were considered significant (*P < 0.05; **P < 0.01).

| RP-HPLC kidneys 37 week old rats | n [animals] | mean CML conc. [%] | SEM [%] | t-test | sign. |
|---|---|---|---|---|---|
| ZDF Placebo | 2 | 100 | 2.00 | 0.010 | * |
| Lean control | 2 | 79 | 0.17 | | |
| ZDF cpd. (II-B) | 2 | 58 | 4.46 | 0.014 | * |
| ZDF cpd. (III-B) | 2 | 93 | 4.77 | 0.298 | |

TABLE 11

Values of the AGE-subtypes CML in the heart of 17-week-old ZDF rats, control rats and ZDF rats treated with the compound of formula (II-B) or the compound of formula (III-B). Values with P < 0.05 were considered significant (*P < 0.05; **P < 0.01).

| RP-HPLC hearts 17 week old rats | n [animals] | mean CML conc. [%] | SEM [%] | t-test | sign. |
|---|---|---|---|---|---|
| ZDF Placebo | 2 | 100 | 3.74 | 0.015 | * |
| Lean control | 2 | 32 | 7.28 | | |
| ZDF cpd. (II-B) | 2 | 26 | 10.95 | 0.025 | * |
| ZDF cpd. (III-B) | 2 | 66 | 3.29 | 0.022 | * |

ZDF rats show significantly higher CML concentration in the kidneys of 17- and 37-week-old rats and in the heart of 17-week-old rats compared to control rats (P<0.05). Treatment with the compound of formula (II-B) reduces the CML concentration in the kidneys of 17- and 37-week-old ZDF rats as well as the CML concentration in the heart of 17-week-old ZDF rats. Compound (III-B) also reduces the CML concentration in kidney and heart of 17-week-old ZDF rats, but not in the kidney of 37-week-old ZDF rats.

The compounds of formula (I) also show insulin sensitizing activity. The prophylactic action of the compounds of the formula (I) upon nephropathy is also indicative that an insulin sensitizing agent can be expected to prevent, reverse, stabilize or retard the progression of microalbuminuria to albuminuria. This is because microalbuminuria is considered to be a predictor of future nephropathy, especially in patients with clinical evidence of pre-diabetic insulin resistance syndrome, alternatively referred to as Syndrome X.

The use of ACE or vasopeptidase inhibitors for the treatment of insulin resistance has not been examined so far.

It has now been found that compounds of formula (I) significantly lower blood glucose concentrations and HbA1c values, and thereby reduce insulin resistance. $HbA_{1c}$ is a measure for long-time glucose values. Glycated $HbA_{1c}$ is an early AGE, a so-called Amadori product.

The effect of the compound of formula (II-B) on $HbA_{1c}$ and blood glucose value is similar to compound (III-B), and both compounds show lower values than the ACE inhibitor ramipril.

Example 6

Blood Glucose and $HbA_{1c}$ Analysis in ZDF Rats

Blood glucose and $HbA_{1c}$ was measured in 10- and 17-week-old male Zucker diabetic fatty rats (Genetic Model Inc.), control rats (Genetic Model Inc.) and male ZDF rats treated for seven weeks with 30 mg/kg/d of compound (II-B), 35 mg/kg/d of compound (III-B) and 1 mg/kg/d ramipril. Fifteen animals were analyzed in each group.

Blood samples for glucose determination were obtained from ZDF rats using standard sampling tubes. Within 30 minutes of collection, samples were separated from the cells by centrifugation. Quantitative determination of blood glucose in serum was performed with an enzymatic in vitro test from Roche Diagnostics GmbH (Gluco-quant, Roche Diagnostics GmbH) using the automated clinical chemistry analyzer Boehringer Mannheim/Hitachi 912.

To obtain blood samples for $HbA_{1c}$ determination, disposable capillary tubes were used. $HbA_{1c}$ values were obtained from hemolyzed whole blood samples with a turbidimetric inhibition immunoassay (Tina-quant, Roche Diagnostics GmbH) and hemoglobin concentrations were determined in a second channel on an automated clinical chemistry analyzer (Boehringer Mannheim/Hitachi 912). $HbA_{1c}$ concentration in percent were calculated from $HbA_{1c}$ to total hemoglobin.

TABLE 12

Blood glucose concentration in 10- and 17-week old ZDF rats, control rats and ZDF rats treated with compound (II-B), compound (III-B) and ramipril.

| blood glucose | ZDF rats | | control | | ZDF Cpd. (II-B) | | ZDF ramipril | | ZDF Cpd. (III-B) | |
|---|---|---|---|---|---|---|---|---|---|---|
| age [weeks] | 10 | 17 | 10 | 17 | 10 | 17 | 10 | 17 | 10 | 17 |
| mean [mM] | 11.92 | 29.68 | 7.32 | 8.04 | 10.67 | 21.09 | 11.74 | 27.33 | 10.37 | 19.74 |
| SEM [mM] | 1.74 | 1.32 | 0.15 | 0.34 | 1.49 | 2.78 | 1.48 | 1.75 | 1.40 | 2.10 |
| n [animals] | 15 | 15 | 20 | 20 | 15 | 15 | 15 | 15 | 15 | 15 |

TABLE 13

HbA$_{1c}$ values in 10- and 17-week old ZDF rats, control rats and ZDF rats
treated with compound (II-B), compound (III-B) and ramipril.

| HbA$_{1c}$ | ZDF rats | | control | | ZDF Cpd. (II-B) | | ZDF ramipril | | ZDF Cpd. (III-B) | |
|---|---|---|---|---|---|---|---|---|---|---|
| age [weeks] | 10 | 17 | 10 | 17 | 10 | 17 | 10 | 17 | 10 | 17 |
| mean [%] | 6.14 | 9.96 | 4.49 | 4.62 | 5.69 | 8.24 | 5.66 | 9.48 | 5.60 | 7.19 |
| SD [%] | 0.22 | 0.42 | 0.02 | 0.02 | 0.16 | 0.71 | 0.14 | 0.52 | 0.15 | 0.46 |
| n [animals] | 15 | 15 | 20 | 20 | 14 | 15 | 15 | 15 | 15 | 15 |

Blood glucose concentration and HbA$_{1c}$ values are significantly lower in the control animals compared to the ZDF rats (P<0.01). The 17-week-old male ZDF rats treated with compound (III-B) or compound (II-B) show also significantly lower blood glucose concentration and HbA$_{1c}$ values compared to the untreated ZDF rats. No significant difference for blood glucose or HbA$_{1c}$ can be shown in ramipril treated 17-week-old ZDF rats compared to the untreated ZDF rats.

Endothelial Dysfunction and Atherosclerotic Plaques

It was shown in the atherogenic rabbit model (White New Zealand rabbits were fed with 0.25% cholesterol plus 3% coconut oil) that even a short 6 week period of an atherogenic diet leads to sustained endothelial dysfunction, even though the animals received a normal diet for 3 months thereafter. In all experiments where the animals were fed constantly during the entire time course with an atherogenic diet, the animals displayed extremely high non-physiologic cholesterol levels that were not comparable to the situation in humans.

The endothelium-dependent relaxation of isolated aortic rings of rabbits as well as the release of nitric oxide and superoxide from endothelial cells serve as measures of endothelial dysfunction. Endothelial dysfunction as well as the atherogenic changes in the blood vessels were both prevented and reversed by to treatment with the ACE/NEP inhibitor compound of formula (II-B), and the data are shown in direct comparison to the ACE inhibitor, ramipril.

Example 7

Effects of Long-term Treatment with the ACE/NEP Inhibitor of the Compound of Formula (I-B) on Endothelial Dysfunction and Atherosclerotic Plaques in Rabbits Fed with an Atherogenic Diet Groups:
Standard: 18 weeks normal diet
Atherogenic: 18 weeks atherogenic diet (3% Coconut oil+ 0.25% Cholesterol)
Varied diet (Var.): 6 weeks atherogenic diet+12 weeks normal diet
Varied Diet+ramipril: 6 weeks atherogenic diet+12 weeks normal diet+ramipril
Varied diet+compound (II-B): 6 weeks atherogenic diet+12 weeks normal diet+cpd. (II-B)

TABLE 14

Relaxation of aortic rings by acetylcholine (ACh) in 4 increasing
concentrations ($10^{-8}$ mol/L, $10^{-7}$ mol/L, $10^{-6}$ mol/L
and $10^{-5}$ mol/L) after preceding stimulation by phenylephrine
($10^{-7}$ mol/L) (data in %; $\bar{x} \pm$ SEM)

| ACh Groups | $10^{-8}$ mol/L | $10^{-7}$ mol/L | $10^{-6}$ mol/L | $10^{-5}$ mol/L |
|---|---|---|---|---|
| Normal Diet | 11.65 ± 1.55 | 52.68 ± 3.06 | 75.64 ± 2.83 | 83.81 ± 3.3 |
| Atherogenic Diet | 2.18 ± 1.23 | 7.07 ± 2.76* # ° † | 11.82 ± 3.88* # ° † | 12.49 ± 4.1* # ° † |
| Var. Diet | 10.76 ± 2.29 | 43.33 ± 3.57† | 63.48 ± 2.89† # ° | 69.41 ± 2.82† # ° |
| Var. + ramipril | 13.08 ± 2.22 | 51.86 ± 4.43 | 77.34 ± 3.7 | 83.73 ± 4.03 |
| Var. + cpd. (II-B) | 19.9 ± 3.48 | 59.62 ± 6.43 | 76.4 ± 6.38 | 80.89 ± 6.82 |

*p < 0.05 vs. Varied diet;
p < 0.05 vs. Normal diet;
°p < 0.05 vs. Var. + ramipril;
†p < 0.05 vs. Var. + cpd. (II-B)

TABLE 15

NO and Superoxide ($O_2^-$) data (in nmol/L; $\bar{x} \pm$ SEM)

| Groups | NO (nM) | $O_2^-$ (nM) |
|---|---|---|
| Normal Diet | 306.71 ± 36.16* | 29.41 ± 5.89 |
| Atherogenic Diet | 167.77 ± 30.65 | 52.12 ± 7.06# |
| Var. Diet | 174.9 ± 25.44 | 35.86 ± 7.49 |
| Var. + ramipril | 368.31 ± 42.25* | 48.09 ± 7.91# |
| Var. + cpd. (II-B) | 329.19 ± 30.10* | 30.18 ± 6.00 |

*p < 0.05 vs. Varied diet, vs. atherogenic diet;
p < 0.05 vs. Varied diet, vs. Normal diet, vs. Varied diet + cpd. (II-B))

NO and $O_2^-$ are markers for endothelial function: increased relaxation and increased NO levels are beneficial, while increased $O_2^-$ formation inhibits the beneficial effects of NO.

What is claimed is:

1. A method of inhibiting both angiotensin converting enzyme and neutral endopeptidase for treatment of a disease amenable to treatment with a compound that inhibits both angiotensin converting enzyme and neutral endopeptidase which comprises administering to a patient in need of said treatment a therapeutically effective amount of a compound of formula (II)

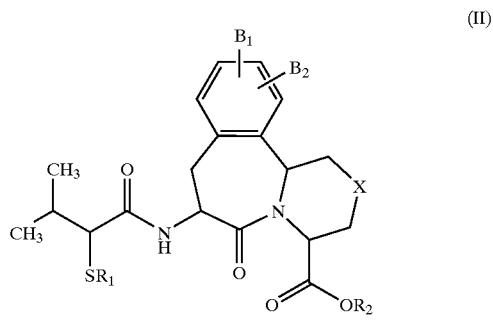

(II)

wherein $R_1$ is hydrogen or acetyl;

$R_2$ is hydrogen, —$CH_2O$—$C(O)C(CH_3)_3$, $C_1$–$C_4$-alkyl, aryl, —($C_1$–$C_4$-alkyl)-aryl, or diphenylmethyl;

X is —$(CH_2)_n$ wherein n is an integer 0 or 1, —S—, —O—,

wherein $R_3$ is hydrogen, $C_1$–$C_4$-alkyl, aryl, or —($C_1$–$C_4$-alkyl)-aryl; and $R_4$ is $CF_3$, $C_1$–$C_{10}$-alkyl, aryl, or —($C_1$–$C_4$-alkyl)-aryl;

$B_1$ and $B_2$ are each independently hydrogen, hydroxy, or —$OR_5$, wherein $R_5$ is $C_1$–$C_4$-alkyl, aryl, or —($C_1$–$C_4$-alkyl)-aryl or, where $B_1$ and $B_2$ are attached to adjacent carbon atoms, $B_1$ and $B_2$ can be taken together with said adjacent carbon atoms to form a benzene ring or methylenedioxy, or a pharmaceutically acceptable salt or stereoisomer thereof, wherein the disease is selected from the group consisting of diabetic nephropathy, insulin resistance, diabetic neuropathy, diabetic retinopathy, myocardial infarction, cataracts, and diabetic cardiomyopathy.

2. The method according to claim 1 wherein the disease is diabetic nephropathy.

3. The method according to claim 1 wherein the disease is insulin resistance.

4. The method according to claim 1 wherein the disease is diabetic neuropathy.

5. The method according to claim 1 wherein the disease is diabetic retinopathy.

6. The method according to claim 1 wherein the disease is myocardial infarction.

7. The method according to claim 1 wherein the disease is cataracts.

8. The method according to claim 1 wherein the disease is diabetic cardiomyopathy.

9. The method according to claim 1, wherein $R_1$ is acetyl.

10. The method according to claim 1, wherein $R_1$ is hydrogen.

11. The method according to claim 1, wherein $B_1$ and $B_2$ are hydrogen.

12. The method according to claim 1, wherein X is —$CH_2$.

13. The method according to claim 1, wherein the compound is the compound of formula (II-A)

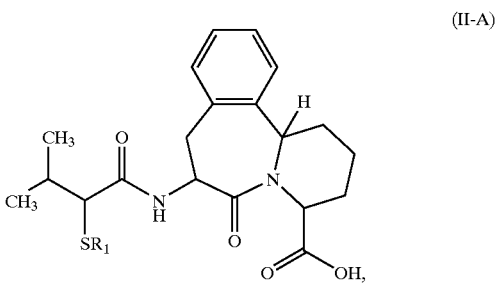

(II-A)

wherein $R_1$ is acetyl or hydrogen.

14. The method according to claim 13, wherein the compound has the formula (II-B)

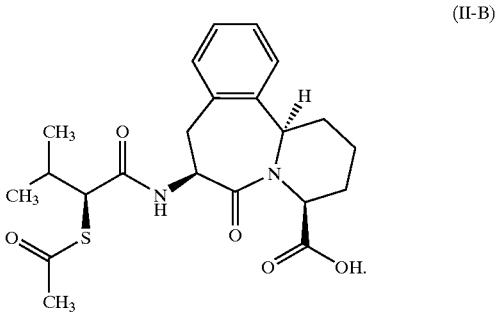

(II-B)

15. The method according to claim 13, wherein the compound has the formula (II-C)

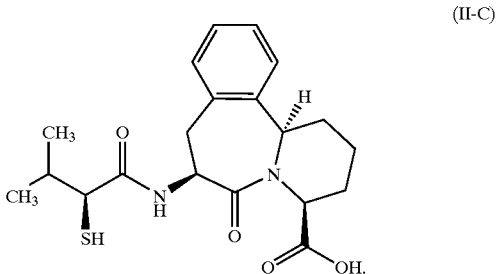

(II-C)

* * * * *